(12) United States Patent
Even et al.

(10) Patent No.: US 7,863,279 B2
(45) Date of Patent: Jan. 4, 2011

(54) TRIAZOLOPYRIDINE CARBOXAMIDE DERIVATIVES AND TRIAZOLOPYRIMIDINE CARBOXAMIDE DERIVATIVES, PREPARATION THEREOF AND THERAPEUTIC USE THEREOF

(75) Inventors: Luc Even, Paris (FR); Christian Hoornaert, Paris (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/577,777

(22) Filed: Oct. 13, 2009

(65) Prior Publication Data

US 2010/0041670 A1 Feb. 18, 2010

Related U.S. Application Data

(63) Continuation of application No. PCT/FR2008/000536, filed on Apr. 16, 2008.

(30) Foreign Application Priority Data

Apr. 18, 2007 (FR) ................................. 07 02808

(51) Int. Cl.
*A61K 31/4353* (2006.01)
*A61K 31/519* (2006.01)
*C07D 471/04* (2006.01)

(52) U.S. Cl. ........................... 514/252.16; 514/253.04; 514/300; 544/254; 544/362; 546/117

(58) Field of Classification Search .................. None
See application file for complete search history.

(56) References Cited

U.S. PATENT DOCUMENTS

2009/0030011 A1* 1/2009 Petry et al. ............. 514/253.04

FOREIGN PATENT DOCUMENTS

| WO | WO 02/055083 | 7/2002 |
|----|--------------|--------|
| WO | WO 2004/035550 | 4/2004 |
| WO | WO 2005/073199 | 8/2005 |
| WO | WO 2006/138657 | 12/2006 |
| WO | WO 2007/045392 | 4/2007 |

OTHER PUBLICATIONS

Fox et al. Expert Opin.Investig.Drugs, vol. 14, p. 695-703 (2005).*
Teare et al.Expert Opin.Investig.Drugs, vol. 14, p. 859-869 (2005).*
Cravatt et al. Current Opinion in Chemical Biology, vol. 7, p. 469-475 (2003).*
Magrioti et al. Bioorganic & Medicinal Chemistry Letters, vol. 18, p. 5424-5427 (2008).*
Parker et al. Physiology & Behavior, vol. 97, p. 121-124 (2009).*
Dinh, T. P., et. al., Brain Monoglyceride Lipase Participating in Endocannabinoid Inactivation, PNAS, (2002), vol. 99, No. 16, pp. 10819-10824.
Dinh, T. P., et al., RNA interference Suggests a Primary Role for Monoacylglycerol Lipase in the Degradation of the Endocannabinoid 2-Arachidonoylglycerol, Molecular Pharmacology, (2004), vol. 66, No. 5, pp. 1260-1264.
Fowler, C. J., et. al., Ibuprofen Inhibits Rat Brain Deamidation of Anandamide at Phamacologically Relevant Concentrations. Mode of Inhibition and Structure-Activity Relationship, The Journal of Pharmacology and Experimental Therapeutics, vol. 283, No. 2, pp. 729-734, (1997).
Karlsson, M., et. al., cDNA Cloning, Tissue Distribution, and Identification of the Catalytic Triad of Monoglyceride Lipase, The Journal of Biological Chemistry, vol. 272, No. 43, pp. 27218-27223, (1997).
Kondo, S., et. al., 2-Arachidonoylglycerol, an Endogenous Cannabinoid Receptor Agonist: Identification as One of the Major Species of Monoacylglycerols in Various Rat Tissues, and Evidence for its Generation Through Ca2+-Dependent and -Independent Mechanisms, FEBS Letters, vol. 429, (1998), pp. 152-156.
Omeir, R. L., et. al., Arachidonoyl Ethanolamide-[1,2-14c] as a Substrate for Anandamide Amidase, Life Sciences, vol. 56, No. 23/24, pp. 1999-2005, (1995).
Saario, S. M., et. al., Monoglyceride Lipase-Like Enzymatic Activity is Responsible for Hydrolysis of 2-Arachidonoylglycerol in Rat Cerebellar Membranes,Biochemical Pharmacology, vol. 67, (2004), pp. 1381-1387.
Savinainen, J. R. . et. al. , Despite Substantial Degradtion, 2-Arachidonoylglycerol is a Potent Full Efficacy Agonist Mediating CB1 Receptor-Dependent G-Protein Activation in Rat Cerebellar Membranes, British Journal of Pharmacology, (2001), vol. 134, pp. 664-672.
Suguira, T., et. al., Biochemistry, Pharmacology and Physiology of 2-Arachidonoylglycerol, an Endogenous Cannabinoid Receptor Ligand , Progress in Lipid Research, vol. 45, (2006) pp. 405-446.

(Continued)

*Primary Examiner*—Emily Bernhardt
(74) *Attorney, Agent, or Firm*—Balaram Gupta; Kelly L. Bender

(57) ABSTRACT

The invention relates to the triazolopyridine carboxamide derivatives and triazolopyrimidine carboxamide derivatives of general formula (I):

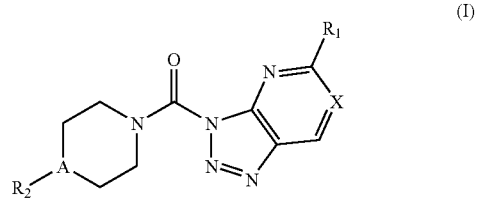

Wherein X, A, $R_1$ and $R_2$ are as defined herein. The invention further relates to preparation methods and therapeutic use thereof.

13 Claims, No Drawings

OTHER PUBLICATIONS

Sugiura, T., et. al., Evidence That 2-Arachidonoylglycerol but Not N-Palmitoylethanolamine or Anandamide is the Physiological Ligand for the Cannabinoid CB2 Receptor, The Journal of Biological Chemistry, vol. 275, No. 1, pp. 605-612, (2000).

Sugiura, T., et. al., Evidence That the Cannabinoid CB1 Receptor is a 2-Arachidonoylglycerol Receptor, The Journal of Biological Chemistry, vol. 274, No. 5, pp. 2794-2801, (1999).

Ueda, N., et. al.,, The Fatty Acid Amide Hydrolase (FAAH), Chemistry and Physics of Lipids, vol. 108, (2000), pp. 107-121.

Rice, K. D., et al., Dibasic Inhibitors of Human Mast Cell Tryptase. Part 1: Synthesis and Optimization of a Novel Class of Inhibitors, Bioorganic & Medicinal Chemistry Letters, vol. 10, (2000), pp. 2357-2360.

Vaughn, J. R., et al., Triazolo and Imidiazopyridines, J. Am. Chem. Soc., (1949), pp. 1885-1887.

* cited by examiner

TRIAZOLOPYRIDINE CARBOXAMIDE DERIVATIVES AND TRIAZOLOPYRIMIDINE CARBOXAMIDE DERIVATIVES, PREPARATION THEREOF AND THERAPEUTIC USE THEREOF

This application is a continuation of International application No. PCT/FR2008/000,536, filed Apr. 16, 2008, which is incorporated herein by reference in its entirety; which claims the benefit of priority of French Patent Application No. 07/02, 808, filed Apr. 18, 2007.

The present invention relates to triazolopyridine carboxamide derivatives and triazolopyrimidine carboxamide derivatives, to the preparation thereof and to the therapeutic use thereof.

The subject of the present invention is the compounds corresponding to formula (I)

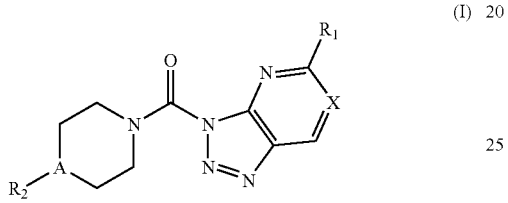

in which:
  A and X are, independently of one another, a nitrogen atom or a CH group,
  $R_1$ is an aryl or heteroaryl group optionally substituted with one or more groups selected from a halogen atom or a $(C_1-C_6)$alkyl, halo$(C_1-C_6)$alkyl, $(C_1-C_6)$alkoxy or halo $(C_1-C_6)$alkoxy group,
  $R_2$ is an aryl group optionally substituted with one or more groups selected from a halogen atom or a methyl, trifluoromethyl, methoxy or trifluoromethoxy group.

The compounds of formula (I) may comprise one or more asymmetric carbon atoms. They may therefore exist in the form of enantiomers or of diastereoisomers. These enantiomers and diastereoisomers, and also mixtures thereof, including racemic mixtures, are part of the invention.

The compounds of formula (I) may exist in the form of bases or of addition salts with acids. Such addition salts are part of the invention.

These salts may be prepared with pharmaceutically acceptable acids, but the salts of other acids that are useful, for example, for purifying or isolating the compounds of formula (I) are also part of the invention.

The compounds of formula (I) may also exist in the form of hydrates or of solvates, i.e. in the form of associations or combinations with one or more molecules of water or with a solvent. Such hydrates and solvates are also part of the invention.

In the context of the present invention:
  the term "$C_{t-z}$", where t and z may take the values from 1 to 7, is intended to mean a carbon-based chain or ring that may contain from t to z carbon atoms; for example, $C_{1-3}$ can characterize a carbon-based chain containing from 1 to 3 carbon atoms;
  the term "a halogen atom" is intended to mean: a fluorine, a chlorine, a bromine or an iodine;
  the term "an alkyl group" is intended to mean: a linear or branched, saturated aliphatic group. By way of examples, mention may be made of methyl, ethyl, propyl, isopropyl, butyl, isobutyl, tert-butyl, pentyl, etc., groups;
  the term "a haloalkyl group" is intended to mean: an alkyl group in which one or more hydrogen atoms has (have) been substituted with a halogen (such as for example fluorine) atom;
  the term "an alkoxy group" is intended to mean: an —O-alkyl radical where the alkyl group is as defined above;
  the term "a haloalkoxy group" is intended to mean: an alkoxy radical in which one or more hydrogen atoms has (have) been substituted with a halogen atom;
  the term "an aryl group" is intended to mean: a cyclic aromatic group containing between 5 and 14 carbon atoms. By way of examples of aryl groups, mention may be made of phenyl or naphthyl;
  the term "a heteroaryl group" is intended to mean: an aromatic heterocyclic group comprising either 5 or 6 carbon atoms and comprising from 1 to 4 heteroatoms, such as nitrogen, oxygen or sulfur. By way of examples of heteroaryl groups, mention may be made of pyrrole, furan, thiophene, pyrazole, imidazole, triazole, tetrazole, oxazole, isoxazole, oxadiazole, thiazole, isothiazole, thiadiazole, pyridine, pyrimidine, pyrazine, pyridazine or triazine.

In the various groups as defined below, the groups A, X, $R_1$ and $R_2$, when they are not defined, have the same definitions as those mentioned above.

Among the compounds of formula (I) which are subjects of the invention, a first group of compounds is constituted of the compounds for which:
  A is a nitrogen atom,
  X is a CH group.

Among the compounds of formula (I) which are subjects of the invention, a second group of compounds is constituted by the compounds for which:
  $R_1$ is an aryl or heteroaryl group optionally substituted with one or more groups selected from a halogen atom or a $(C_1-C_6)$alkyl, halo$(C_1-C_6)$alkyl, $(C_1-C_6)$alkoxy or halo $(C_1-C_6)$alkoxy group.

Among the compounds of formula (I) which are subjects of the invention, a third group of compounds is constituted of the compounds for which:
  $R_1$ is a phenyl, furan, thiophene or naphthalene group, optionally substituted with a halogen atom.

The combinations of the groups one to three as defined above are also part of the invention.

Among the compounds of formula (I) which are subjects of the invention, mention may in particular be made of the following compounds:
  [5-(2-chlorophenyl)[1,2,3]triazolo[4,5-b]pyridin-3-yl][4-(3-trifluoromethylphenyl)piperazin-1-yl]methanone;
  [5-(3-chlorophenyl)[1,2,3]triazolo[4,5-b]pyridin-3-yl][4-(3-trifluoromethylphenyl)piperazin-1-yl]methanone;
  [5-(4-chlorophenyl)[1,2,3]triazolo[4,5-b]pyridin-3-yl][4-(3-trifluoromethylphenyl)piperazin-1-yl]methanone;
  (5-furan-3-yl[1,2,3]triazolo[4,5-b]pyridin-3-yl)[4-(3-trifluoromethylphenyl)piperazin-1-yl]methanone;
  (5-thiophen-3-yl[1,2,3]triazolo[4,5-b]pyridin-3-yl)[4-(3-trifluoromethylphenyl)piperazin-1-yl]methanone;
  (5-naphthalen-2-yl[1,2,3]triazolo[4,5-b]pyridin-3-yl)[4-(3-trifluoromethylphenyl)piperazin-1-yl]methanone;
  b 5-naphthalen-1-yl[1,2,3]triazolo[4,5-b]pyridin-3-yl)[4-(3-trifluoromethylphenyl)piperazin-1-yl]methanone.

In the subsequent text, the term "protective group Pg" is intended to mean a group which makes it possible, on the one hand, to protect a reactive function such as a hydroxyl or an amine during a synthesis and, on the other hand, to regenerate the intact reactive function at the end of synthesis. Examples of protective groups and also methods of protection and deprotection are given in "Protective Groups in Organic Synthesis", Green et al., 2$^{nd}$ Edition (John Wiley & Sons, Inc., New York), 1991.

In the subsequent text, the term "leaving group" is intended to mean a group that can be readily cleaved from a molecule by breaking a heterolytic bond, with the departure of a pair of electrons. This group can thus be readily replaced with another group during a substitution reaction, for example. Such leaving groups are, for example, halogens or an activated hydroxyl group, such as a methanesulfonate, benzenesulfonate, p-toluenesulfonate, triflate, acetate, etc. Examples of leaving groups and also references for the preparation thereof are given in "Advances in Organic Chemistry", J. March, 3$^{rd}$ Edition, Wiley Interscience, 1985, p. 310-316.

In accordance with the invention, the compounds of general formula (I) can be prepared according to the process illustrated in scheme 1 which follows.

According to pathway A, in a first stage, the compounds of general formula (II), in which X is as defined above, are converted to compounds of general formula (III), in which X and $R_1$ are as defined above. The conversion is carried out by means of a coupling reaction with a boronic acid or a boronate of respective general formula (IV) or (V), in which $R_1$ is as defined above, and $(OR'')_2$ is a pinacol group, catalyzed by a palladium complex. In a second stage, the compounds of general formula (III), in which X and $R_1$ are as defined above, are converted to compounds of general formula (VI), in which $R_1$, $R_2$, X and A are as defined above, by reaction with a carbamoyl chloride of general formula (VII). The reaction is carried out in a solvent such as N,N-dimethylformamide or N-methylpyrrolidone, in the presence of a base such as sodium hydride, potassium tert-butoxide or potassium tert-pentoxide.

In a third stage, the compounds of general formula (VI) are converted to compounds of general formula (VIII), in which $R_2$, A, $R_1$ and X are as defined above, by reduction of the nitro group to an amino group. The reaction can be carried out by various methods described in the literature or known to those skilled in the art, for instance hydrogenation in the presence of a catalyst based on palladium, platinum or nickel and variants thereof.

In the fourth stage, the compounds of general formula (VIII) are converted to compounds of general formula (I) by means of a diazotization/ring-closure reaction. The reaction can be carried out using a nitrite, for example sodium nitrite or potassium nitrite in an acidic medium or isoamyl nitrite or tert-butyl nitrite, in solvents such as water or tetrahydrofuran or a mixture thereof.

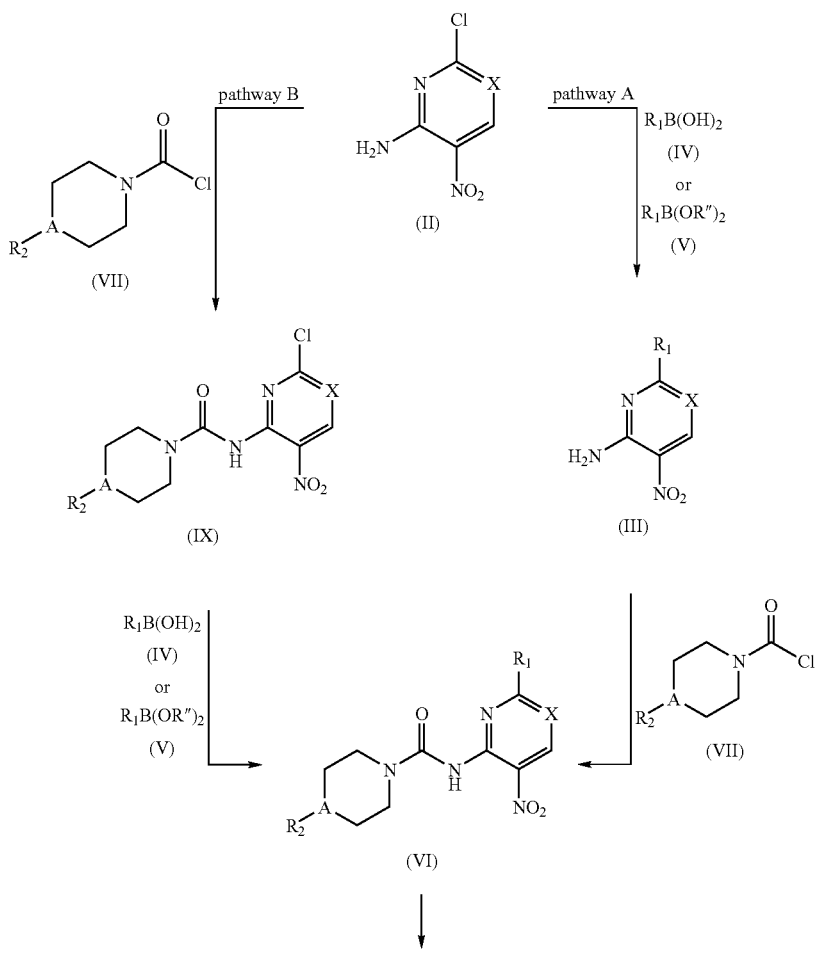

Scheme 1

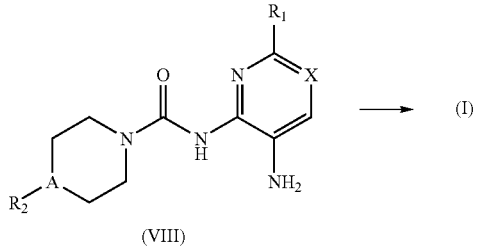

Pathway B of scheme 1 illustrates an alternative method for preparing the compounds of formula (I).

In a first stage, the compounds of general formula (II) are converted to compounds of general formula (IX) by reaction with a carbamoyl chloride of general formula (VII) as defined above. In a second stage, the compounds of general formula (IX) are converted to compounds of general formula (VI) by reaction with a boronic acid or a boronate of general formula (IV) or (V), as defined above. The compounds of general formula (VI) are subsequently converted to compounds of general formula (VIII) and then to compounds of general formula (I) as specified above.

The compounds of general formulae (II), (IV) and (V) are commercially available. The carbamoyl chlorides of general formula (VII), if they are not commercially available, can be prepared by any method described in the literature or known to those skilled in the art, for example starting from the corresponding amines by reaction with phosgene, diphosgene or triphosgene.

The examples which follow illustrate the preparation of some compounds of the invention. These examples are not limiting, and merely illustrate the invention. The microanalyses, the IR and NMR spectra and/or the LC-MS confirm the structures and the purities of the compounds obtained. The melting points (Mp) are indicated in degrees Celsius.

EXAMPLE 1

Compound No. 3 of the Table

[5-(4-chlorophenyl)[1,2,3]triazolo[4,5-b]pyridin-3-yl][4-(3-trifluoromethylphenyl)piperazin-1-yl]methanone 1.1. 4-(3-trifluoromethylphenyl)piperazine-1-carboxylic acid, (6-chloro-3-nitropyridin-2-yl)amide Pathway B:

Under an argon atmosphere, 0.55 g (13.83 mmol) of sodium hydride at 60% in oil is added portionwise to a solution of 1 g (5.76 mmol) of 2-amino-6-chloro-3-nitropyridine and 2 g (6.91 mmol) of 4-(3-trifluoromethylphenyl)-1-piperazinecarbonyl chloride (prepared from 1-(3-trifluoromethylphenyl)-piperazine and triphosgene) in 11 ml of dimethylformamide cooled with an ice bath. Stirring of the reaction medium is continued at the temperature of the ice bath for 15 minutes and then at ambient temperature for 2 hours. The mixture is cooled with an ice bath and 40 ml of a 1M aqueous solution of hydrochloric acid are added dropwise. 40 ml of ethyl acetate are added and the mixture is stirred vigorously for 15 minutes. The resulting mixture is adjusted to basic pH by adding a 1M aqueous solution of sodium hydroxide. The organic phase is separated by settling out and washed with 25 ml of water and 25 ml of a saturated aqueous solution of sodium chloride. The resulting product is dried over sodium sulfate and evaporated to dryness. The product is purified by silica gel chromatography, elution being carried out with an 80:20 then 60:40 mixture of cyclohexane and ethyl acetate. 1.54 g (yield: 62%) of product are obtained in the form of an orange gum.

$^1$H NMR (DMSO-$d_6$, δ ppm): 8.65 (d, 1H), 7.40-7.75 (m+d, 4H), 7.35 (d, 1H), 3.90 (m, 4H), 3.50 (m, 4H).

1.2. 4-(3-trifluoromethylphenyl)piperazine-1-carboxylic acid, [6-(4-chloro-phenyl)-3-nitropyridin-2-yl]amide Pathway B:

Under a nitrogen atmosphere, 0.64 g (1.50 mmol) of 4-(3-trifluoromethylphenyl)piperazine-1-carboxylic acid, (6-chloro-3-nitropyridin-2-yl)amide obtained in stage 1.1. (pathway B) is mixed with 0.33 g (2.1 mmol) of 4-chlorobenzeneboronic acid, 1.87 ml (3.75 mmol) of a 2M aqueous solution of sodium carbonate and 0.18 g (4.26 mmol) of lithium chloride in 100 ml of a pre-degassed mixture of ethanol/toluene/water (v/v: 1/1/0.4). 0.08 g (0.07 mmol) of tetrakis(triphenylphosphine)palladium(0) is added. The mixture is heated at 90° C. with stirring for 8 hours. The mixture is cooled to ambient temperature and then diluted with 50 ml of dichloromethane and 25 ml of water. The organic phase is separated by settling out and washed with 25 ml of water and 25 ml of a saturated solution of sodium chloride. The resulting product is dried over sodium sulfate and evaporated to dryness. The product is purified by silica gel chromatography, elution being carried out with an 80:20 then 60:40 mixture of cyclohexane and ethyl acetate. 0.6 g (yield: 79%) of product is obtained in the form of an oil.

$^1$H NMR (DMSO-$d_6$, δ ppm): 8.55 (d, 1H), 8.30 (d, 2H), 8.00 (d, 1H), 7.80 (d, 2H), 7.80 (m, 1H), 7.60 (m, 1H), 7.40 (m, 2H), 7.20 (m, 1H), 3.8 (m, 4H), 3.50 (m, 4H).

Pathway A: alternatively, the 4-(3-trifluoromethylphenyl)piperazine-1-carboxylic acid, [6-(4-chlorophenyl)-3-nitropyridin-2-yl]amide can be prepared as follows.

Under a nitrogen atmosphere, 1 g (5.76 mmol) of 2-amino-6-chloro-3-nitropyridine is mixed with 1.26 g (8.07 mmol) of 4-chlorobenzeneboronic acid, 7.2 ml (14.4 mmol) of a 2M aqueous solution of sodium carbonate and 0.7 g (16.36 mmol) of lithium chloride in 44 ml of a pre-degassed mixture of ethanol/toluene/water (v/v: 1/1/0.4). 0.34 g (0.29 mmol) of tetrakis(triphenylphosphine)palladium(0) is added. The mixture is heated at 90° C. with stirring for 18 hours. The resulting mixture is cooled to ambient temperature and then diluted with 50 ml of dichloromethane and 25 ml of water. The organic phase is separated by settling out and washed with 25 ml of water and 25 ml of a saturated solution of sodium chloride. The resulting product is dried over sodium sulfate and evaporated to dryness. The product is purified by silica gel chromatography, elution being carried out with a 50:50 then 80:20 mixture of dichloromethane and cyclohexane. 0.395 g (yield: 27%) of 6-(4-chlorophenyl)-3-nitropyridin-2-ylamine is obtained in the form of a white powder.

LC-MS (m/z): 250 (MH$^+$)

$^1$H NMR (DMSO-d$_6$, δ ppm): 8.45 (d, 1H), 8.15 (d, 1H), 7.95 (m, 2H), 7.60 (d, 1H), 7.30 (d, 1H), 7.20 (d, 1H).

This product is used as in stage 1.1 in order to obtain the 4-(3-trifluoromethylphenyl)piperazine-1-carboxylic acid, [6-(4-chlorophenyl)-3-nitropyridin-2-yl]amide.

1.3. 4-(3-(trifluoromethylphenyl)piperazine-1-carboxylic acid, [3-amino-6-(4-chlorophenyl)pyridin-2-yl]amide In a hydrogenation flask, 0.72 g (1.44 mmol) of 4-(3-trifluoromethylphenyl)piperazine-1-carboxylic acid, [6-(4-chlorophenyl)-3-nitropyridin-2-yl]amide, obtained in stage 1.2 (pathway A or B), is dissolved in a mixture of 250 ml of ethanol and 1.44 ml of a 1M aqueous solution of hydrochloric acid (1.44 mmol). 0.13 g of platinum (0.72 mmol) at 10% on charcoal is added. The mixture is stirred under a hydrogen atmosphere at a pressure of 40 Psi (2.5 bar) for 2 hours. 5 ml of a 5N solution of hydrochloric acid in isopropanol are added, the mixture is filtered through celite and washing is carried out with ethanol. The filtrate is evaporated so as to obtain 0.57 g (yield: 84%) of product in the form of a red powder.

LC-MS (m/z): 476 (MH$^+$)

$^1$H NMR (DMSO-d$_6$, δ ppm): 7.90 (d, 2H), 7.65 (d, 2H), 7.50 (m, 3H), 7.35 (m, 1H), 7.20 (m, 2H), 7.00 (m, 1H), 3.60 (m, 4H), 3.25 (m, 4H).

1.4. [5-(4-chlorophenyl)[1,2,3]triazolo[4,5-b]pyridin-3-yl][4-(3-trifluoromethylphenyl)piperazin-1-yl]methanone In a 100 ml three-necked flask, 0.55 g (1.17 mmol) of 4-(3-trifluoromethylphenyl)piperazine-1-carboxylic acid, [3-amino-6-(4-chlorophenyl)pyridin-2-yl]amide, obtained in stage 1.3, is dissolved in a mixture of 5 ml of water and 5 ml of 37% aqueous hydrochloric acid, cooled in an ice bath. Using a dropping funnel, 0.24 g (3.50 mmol) of sodium nitrite dissolved in 4 ml of water is added dropwise. The mixture is stirred for 2 hours at 0° C. It is left to stand for one hour in the ice bath and then the solid is filtered off. It is washed with 3×10 ml of water so as to obtain a beige solid. The latter is dried under vacuum in the presence of phosphorus pentoxide. The product is purified by silica gel chromatography, elution being carried out with an 80:20 then 60:40 mixture of cyclohexane and ethyl acetate. The oil obtained is crystallized from pentane so as to obtain 0.15 g (yield: 26%) of product in the form of a light yellow powder.

Melting point (° C.): 139-141° C.

LC-MS (m/z): 487 (MH$^+$)

IR (KBr, cm$^{-1}$): 1718, 1591

$^1$H NMR (DMSO-d$_6$, δ ppm): 8.80 (d, 1H), 8.25 (dd, 3H), 7.60 (d, 2H), 7.45 (t, 1H), 7.25 (d, 1H), 7.20 (s, 1H), 7.10 (d, 1H), 3.30-4.00 (m, 8H).

Table 1 which follows illustrates the chemical structures and the physical properties of some examples of compounds according to the invention. In this table:

in the "salt" column, "—" represents a compound in the form of a free base, whereas "HCl" represents a compound in hydrochloride form;

Ph represents a phenyl group.

TABLE 1

(I)

| No. | R1 | R2 | X | A | Salt | Mp (° C.) (Melting point) |
|---|---|---|---|---|---|---|
| 1 | 2-Cl-Ph | 3-CF$_3$—Ph | CH | N | — | 69-71 |
| 2 | 3-Cl-Ph | 3-CF$_3$—Ph | CH | N | — | 102-104 |
| 3 | 4-Cl-Ph | 3-CF$_3$—Ph | CH | N | — | 139-141 |
| 4 | furan-3-yl | 3-CF$_3$—Ph | CH | N | — | 68-70 |
| 5 | thien-2-yl | 3-CF$_3$—Ph | CH | N | — | 93-95 |
| 6 | naphthalen-1-yl | 3-CF$_3$—Ph | CH | N | — | 90-92 |
| 7 | naphthalen-1-yl | 3-CF$_3$—Ph | CH | N | — | 80-82 |

The compounds according to the invention surprisingly exhibit an inhibitory effect on the MGL (monoacyl glycerol lipase) enzyme. The MGL enzyme catalyzes the hydrolysis of endogenous derivatives of monoglyceride esters of various fatty acids (FEBS Letters 1998, 429, 152-156) and in particular the hydrolysis of 2-arachidonoylglycerol (2-AG) and of 1(3)-arachidonoylglycerol (1(3)-AG) (J. Biol. Chem. 1987, 272 (48), 27218-27223; Proc. Natl. Acad. Sci. USA 2002, 99 (16), 10819-10824; Biochem. Pharmacol. 2004, 67, 1381-1387; Mol. Pharmacol. 2004, 66 (5), 1260-1264). The 2-AG and 1(3)-AG derivatives in particular interact with cannabinoid receptors (J. Biol. Chem. 1999, 274 (5), 2794-2801; J. Biol. Chem. 2000, 275 (1), 605-612; British J. Pharmacol. 2001, 134, 664-672).

The compounds of the invention block this degradation pathway and increase the tissue levels of these derivatives, and in particular of 2-AG and/or of 1(3)-AG. In this respect, they can be used in the prevention and treatment of pathological conditions in which 2-AG and/or 1(3)-AG in particular, and/or any other substrate metabolized by the MGL enzyme, is (are) involved (Progress Lipid Research 2006, 45, 405-446).

The compounds according to the invention may also additionally have an inhibitory effect on the FAAH (Fatty Acid Amide Hydrolase) enzyme. The FAAH enzyme (*Chemistry and Physics of Lipids* (2000), 108, 107-121) catalyzes the hydrolysis of endogenous derivatives of amides and of esters of various fatty acids, such as N-arachidonoylethanolamine (anandamide), N-palmitoylethanolamine, N-oleoylethanolamine or oleamide. These derivatives exercise various pharmacological activities by interacting, inter alia, with cannabinoid and vanilloid receptors.

The compounds of the invention block this degradation pathway and increase the tissue levels of these endogenous substances. In this respect, they can be used in the prevention and treatment of pathological conditions in which endogenous cannabinoids and/or any other substrate metabolized by the FAAH enzyme is (are) involved.

Tests comprised measuring the activity, in vitro, of the compounds of the invention on the MGL enzyme.

The inhibitory activity was measured in a radioenzymatic assay based on measuring the product of hydrolysis of 2-oleoyl glycerol ([$^3$H] 2-OG) by MGL. The products of hydrolysis of [$^3$H] 2-OG, labeled on the glycerol, are oleic acid and [$^3$H] glycerol, and the source of MGL enzyme is a homogenate of mouse brain from which the cerebellum and the medulla oblongata have been removed. The mouse brains are removed, and stored at −80° C. until they are used, or homogenized immediately for twice 5 seconds using a Precellys apparatus at 5000 rpm (Bertin) in a 10 mM Tris-HCl, 150 mM NaCl, 1 mM EDTA buffer (pH 8) at 4° C. The concentration of the homogenates is then adjusted to 7.5 µg/µl.

The dilution series of the compounds is prepared from stock solutions at 20 mM in 100% DMSO. The first dilution of this series is prepared in 100% DMSO and then the second is prepared in the enzyme reaction buffer (50 mM phosphate, 0.1% BSA) leading to the preparation of a 10-times concentrated concentration range. The test compounds are preincubated at the selected concentration, for 20 minutes, with the mouse brain homogenate preparation. The final concentration of DMSO in the enzyme reaction does not exceed 0.1%.

Assaying of the MGL activity is carried out in a 96-well microplate in a final reaction volume of 100 µl. Briefly, 75 µg of proteins, preincubated with the test compounds, are diluted in 50 mM of phosphate buffer containing 0.1% BSA, and incubated, for 20 minutes at ambient temperature, in the presence of 50 µM of 2-OG containing an amount of [$^3$H] 2-OG of 0.027 µCi/well (specific activity of 20 Ci/mmol). The reaction is stopped and the products formed are separated by adding and mixing 100 µl of chloroform/methanol (1/1). After stirring for 10 minutes, the microplate is centrifuged for 15 minutes at 4000 g and a 30 µl aliquot of the aqueous phase containing the [$^3$H] glycerol produced is removed and then counted for 5 minutes by liquid scintillation (Wallac 1450 Microbeta).

The inhibitory activity with respect to MGL is given by the concentration which inhibits 50% of the activity of MGL.

Under these conditions, the most active compounds of the invention exhibit an IC$_{50}$ (concentration inhibiting 50% of the control enzyme activity of MGL) of between 0.001 and 0.1 µM.

For example, compounds Nos. 3 and 5 showed an IC$_{50}$ of 0.002 and 0.007 µM, respectively.

Tests comprised measuring the activity, in vitro, of the compounds of the invention on the FAAH enzyme.

The inhibitory activity was measured in a radioenzymatic assay based on measuring the product of hydrolysis (ethanolamine [1-3H]) of anandamide by FAAH (Life Science (1995), 56, 1999-2005 and Journal of Pharmacology and Experimented Therapeutics (1997), 283, 729-734). The products of hydrolysis of [$^3$H] anandamide, labeled on ethanolamine, are arachidonic acid and [$^3$H]ethanolamine, and the source of FAAH enzyme is a homogenate of mouse brain from which the cerebellum and the medulla oblongata have been removed. The mouse brains are removed, and stored at −80° C. until they are used, or homogenized immediately for twice 5 seconds using a Precellys apparatus at 5000 rpm (Bertin) in a 10 mM Tris-HCl, 150 mM NaCl, 1 mM EDTA buffer (pH 8) at 4° C. The concentration of the homogenates is then adjusted to 20 µg/µl.

The dilution series of the compounds is prepared from stock solutions at 20 mM in 100% DMSO. The first dilution of this series is prepared in 100% DMSO, then the second is prepared in the enzyme reaction buffer (10 mM Tris-HCl, 150 mM NaCl, 1 mM EDTA (pH 8), 0.1% BSA) leading to the preparation of a 10-times concentrated concentration range. The test compounds are preincubated at the selected concentration for 20 minutes with the mouse brain homogenate preparation. The final concentration of DMSO in the enzyme reaction does not exceed 0.1%.

Assaying of the FAAH activity is carried out in a 96-well microplate in a final reaction volume of 70 µl. Briefly, 200 µg of mouse brain homogenate, preincubated with the test compounds, are diluted in 10 mM Tris-HCl, 150 mM NaCl, 1 mM EDTA (pH 8) containing 0.1% of BSA and incubated, for 20 minutes at ambient temperature, in the presence of 10 µM of anandamide containing an amount of [$^3$H]-anandamide of 0.01 µCi/well (specific activity of 60 Ci/mmol). The reaction is stopped and the products formed are separated by adding and mixing 140 µl of chloroform/methanol (2/1). After stirring for 10 minutes, the microplate is centrifuged for 15 minutes at 4000 g and a 30 µl aliquot of the aqueous phase containing the [$^3$H]ethanolamine produced is removed and then counted for 5 minutes by liquid scintillation (Wallac 1450 Microbeta).

Under these conditions, the most active compounds of the invention exhibit an IC$_{50}$ (concentration inhibiting 50% of the control enzyme activity of FAAH) of between 0.001 and 0.1 µM.

For example, compound No. 3 showed an IC$_{50}$ of 0.002 µM.

It therefore appears that the compounds according to the invention have an inhibitory activity which is selective with respect to MGL or mixed with respect to MGL and FAAH.

The compounds according to the invention can therefore be used for the preparation of medicaments, in particular of medicaments which inhibit the MGL enzyme or the MGL and FAAH enzymes.

Thus, according to another of its aspects, a subject of the invention is medicaments which comprise a compound of formula (I), or an addition salt of the latter with a pharmaceutically acceptable acid, or else a hydrate or a solvate of the compound of formula (I).

These medicaments find use in therapeutics, in particular in the treatment and prevention of:
  pain, in particular acute or chronic pain of neurogenic type: migraine, neuropathic pain including forms associated with the herpes virus and with diabetes;
  acute or chronic pain associated with inflammatory diseases: arthritis, rheumatoid arthritis, osteoarthritis, spondylitis, gout, vasculitis, Crohn's disease, irritable bowel syndrome;
  acute or chronic peripheral pain;
  dizziness, vomiting, nausea, in particular subsequent to chemotherapy;
  eating disorders, in particular anorexia and cachexia of various natures;
  metabolic syndrome and manifestations thereof, including obesity;
  dyslipidemia and manifestations thereof, including atherosclerosis and coronary diseases;
  neurological and psychiatric pathological conditions: shaking, dyskinesia, dystonia, spasticity, obsessive-compulsive behavior, Tourette's syndrome, all forms of depression and anxiety of any nature or origin, mood disorders, psychoses;
  acute and chronic neurodegenerative diseases: Parkinson's disease, Alzheimer's disease, senile dementia, Huntington's chorea, lesions associated with cerebral ischemia and with cranial and medullary trauma, amyotrophic lateral sclerosis;
  epilepsy;
  sleep disorders, including sleep apnea;

cardiovascular diseases, in particular hypertension, cardiac arrhythmias, arteriosclerosis, heart attack, cardiac ischemia;

renal ischemia;

cancers: benign skin tumors, brain tumors and papillomas, prostate tumors, brain tumors (glioblastomas, medulloepitheliomas, medulloblastomas, neuroblastomas, tumors of embryonic origin, astrocytomas, astroblastomas, ependyomas, oligodendrogliomas, plexus tumors, neuroepitheliomas, epiphyseal tumors, ependymoblastomas, malignant meningiomas, sarcomatosis, malignant melanomas, schwannomas);

immune system disorders, in particular autoimmune diseases: psoriasis, lupus erythematosus, diseases of the connective tissue or collagen diseases, Sjögren's syndrome, ankylosing spondylarthritis, undifferentiated spondylarthritis, Behcet's disease, hemolytic autoimmune anemias, multiple sclerosis, amyotrophic lateral sclerosis, amyloses, transplant rejection, diseases affecting the plasmocytic line;

allergic diseases: immediate or delayed hypersensitivity, allergic rhinitis or conjunctivitis, contact dermatitis;

parasitic, viral or bacterial infectious diseases: AIDS, meningitis;

inflammatory diseases, in particular diseases of the joints: arthritis, rheumatoid arthritis, osteoarthritis, spondylitis, gout, vasculitis, Crohn's disease, irritable bowel syndrome;

osteoporosis;

ocular conditions: ocular hypertension, glaucoma;

pulmonary conditions: respiratory tract diseases, bronchospasms, coughing, asthma, chronic bronchitis, chronic obstructive airway disease, emphysema;

gastrointestinal diseases: irritable bowel syndrome, intestinal inflammatory disorders, ulcers, diarrhea;

urinary incontinence and bladder inflammation.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected, according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or a possible salt, solvate or hydrate thereof, can be administered in unit administration form, as a mixture with conventional pharmaceutical excipients, to animals and to human beings for the prophylaxis or treatment of the disorders or diseases above.

Suitable unit administration forms comprise oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathological conditions indicated above, which comprises the administration of an effective dose of a compound according to the invention, or a pharmaceutically acceptable salt or hydrate or solvate thereof, to a patient.

What is claimed is:

1. A compound of the formula (I):

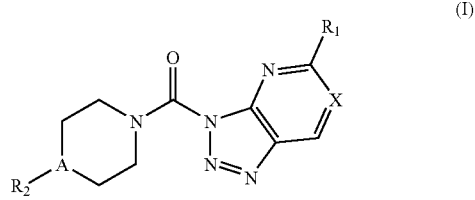

in which:

A and X are, independently of one another, nitrogen or CH;

$R_1$ is an aryl or heteroaryl group optionally substituted with one or more groups selected from halogen, $(C_1-C_6)$ alkyl, halo$(C_1-C_6)$alkyl, $(C_1-C_6)$alkoxy and halo$(C_1-C_6)$ alkoxy and wherein said heteroaryl group is selected from the group consisting of pyrrole, furan, thiophene, pyrazole, imidazole, triazole, tetrazole, oxazole, isoxazole, oxadiazole, thiazole, isothiazole and thiadiazole; and $R_2$ is an aryl group optionally substituted with one or more groups selected from halogen, methyl, trifluoromethyl, methoxy and trifluoromethoxy; or a salt thereof.

2. The compound of formula (I) according to claim 1, wherein:

A is nitrogen; and

X is CH; or a salt thereof

3. The compound of formula (I) according to claim 1, wherein:

$R_1$ is an aryl or heteroaryl group optionally substituted with one or more groups selected from halogen, $(C_1-C_6)$ alkyl, halo$(C_1-C_6)$alkyl, $(C_1-C_6)$alkoxy and halo$(C_1-C_6)$ alkoxy and wherein said heteroaryl group is selected from the group consisting of pyrrole, furan, thiophene, oxazole, isoxazole, thiazole and isothiazole; or a salt thereof.

4. The compound of formula (I) according to claim 1, wherein:

$R_1$ is phenyl, furan, thiophene or naphthalene, optionally substituted with halogen, or a salt thereof.

5. The compound of formula (I) according to claim 1, which is selected from the group consisting of:

[5-(2-chlorophenyl)[1,2,3]triazolo[4,5-b]pyridin-3-yl][4-(3-trifluoromethylphenyl) piperazin-1-yl]methanone;
[5-(3-chlorophenyl)[1,2,3]triazolo[4,5-b]pyridin-3-yl][4-(3-trifluoromethylphenyl) piperazin-1-yl]methanone;
[5-(4-chlorophenyl)[1,2,3]triazolo[4,5-b]pyridin-3-yl][4-(3-trifluoromethylphenyl) piperazin-1-yl]methanone;
(5-furan-3-yl[1,2,3]triazolo[4,5-b]pyridin-3-yl)[4-(3-trifluoromethylphenyl) piperazin-1-yl]methanone;
(5-thiophen-3-yl[1,2,3]triazolo[4,5-b]pyridin-3-yl)[4-(3-trifluoromethylphenyl) piperazin-1-yl]methanone;
(5-naphthalen-2-yl[1,2,3]triazolo[4,5-b]pyridin-3-yl)[4-(3-trifluoromethylphenyl) piperazin-1-yl]methanone; and
(5-naphthalen-1-yl[1,2,3]triazolo[4,5-b]pyridin-3-yl)[4-(3-trifluoromethylphenyl) piperazin-1-yl]methanone.

6. A process for preparing a compound of formula (I) according to claim 1, comprising:
converting a compound of formula (VIII):

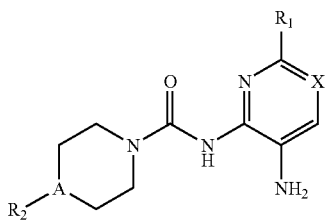

(VIII)

in which $R_1$, $R_2$, X and A are as defined in claim 1, to a compound of formula (I), by means of a diazotization/ring-closure reaction, under the action of a nitrite.

7. A pharmaceutical composition comprising a compound of formula (I) according to claim 1 or a pharmaceutically acceptable salt thereof and at least one pharmaceutically acceptable excipient.

8. A pharmaceutical composition comprising a compound of formula (I) according to claim 2 or a pharmaceutically acceptable salt thereof and at least one pharmaceutically acceptable excipient.

9. A pharmaceutical composition comprising a compound of formula (I) according to claim 3 or a pharmaceutically acceptable salt thereof and at least one pharmaceutically acceptable excipient.

10. A pharmaceutical composition comprising a compound of formula (I) according to claim 4 or a pharmaceutically acceptable salt thereof and at least one pharmaceutically acceptable excipient.

11. A pharmaceutical composition comprising a compound of formula (I) according to claim 5 or a pharmaceutically acceptable salt thereof and at least one pharmaceutically acceptable excipient.

12. A method of treatment of acute or chronic pain comprising administering to said patient a therapeutically effective amount of a compound of formula (I) according to claim 1 or a pharmaceutically acceptable salt thereof.

13. A method of treatment of a disease selected from the group consisting of vomiting and nausea, comprising administering to said patient a therapeutically effective amount of a compound of formula (I) according to claim 1 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,863,279 B2 | Page 1 of 1 |
| APPLICATION NO. | : 12/577777 | |
| DATED | : January 4, 2011 | |
| INVENTOR(S) | : Luc Even et al. | |

It is certified that error appears in the above-identified patent and that said Letters Patent is hereby corrected as shown below:

In column 2, line 63, delete "b 5-" and insert -- 5- --, therefor.

In column 12, line 51, in claim 2, after "thereof" insert -- . --.

Signed and Sealed this
Thirteenth Day of September, 2011

David J. Kappos
*Director of the United States Patent and Trademark Office*